United States Patent [19]

Lidman et al.

[11] Patent Number: 5,662,694
[45] Date of Patent: Sep. 2, 1997

[54] MAGNETIC FIELD DETECTOR

[75] Inventors: Johan Lidman, Stockholm; Kenth Nilsson, Akersberga, both of Sweden

[73] Assignee: Pacesetter AB, Solna, Sweden

[21] Appl. No.: 572,068

[22] Filed: Dec. 14, 1995

[30] Foreign Application Priority Data

Dec. 15, 1994 [SE] Sweden ................................. 9404374

[51] Int. Cl.$^6$ ........................................................ A61N 1/02
[52] U.S. Cl. ............................................................... 607/60
[58] Field of Search ............................. 607/27–32, 59–60

[56] References Cited

U.S. PATENT DOCUMENTS 4,541,431  9/1985  Ibrahim et al. .
4,611,127  9/1986  Ibrahim et al. .

FOREIGN PATENT DOCUMENTS 0 670 170  9/1995  European Pat. Off. .
35 25 070  9/1991  Germany .

*Primary Examiner*—William E. Kamm
*Attorney, Agent, or Firm*—Hill, Steadman & Simpson

[57] ABSTRACT

In a magnetic field detector as well as in a combined telemetry and magnetic field detector unit in a medical implant, a magnetic field sensor with a coil and a diode are employed for determining the presence of a magnetic field. For making such a determination, the coil is charged by a source of voltage for a defined period of time, the time for the discharge of the coil through the diode depending on whether a magnetic field is present. A detection signal indicating the presence of a magnetic field is generated if the discharge time is less than a defined time threshold value.

7 Claims, 4 Drawing Sheets

FIG. 3
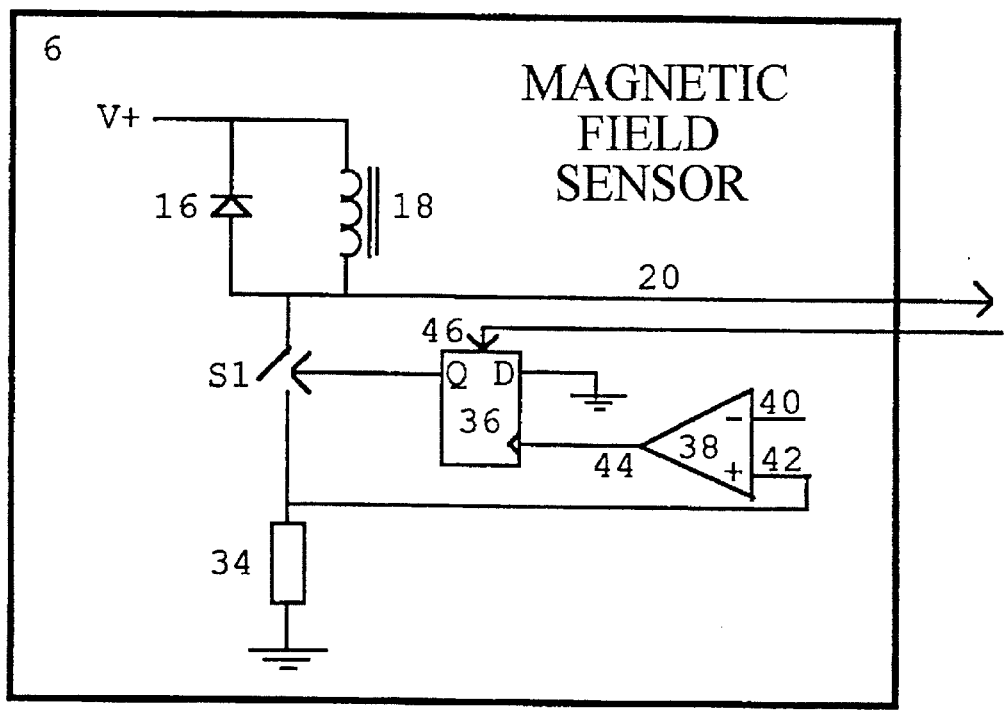
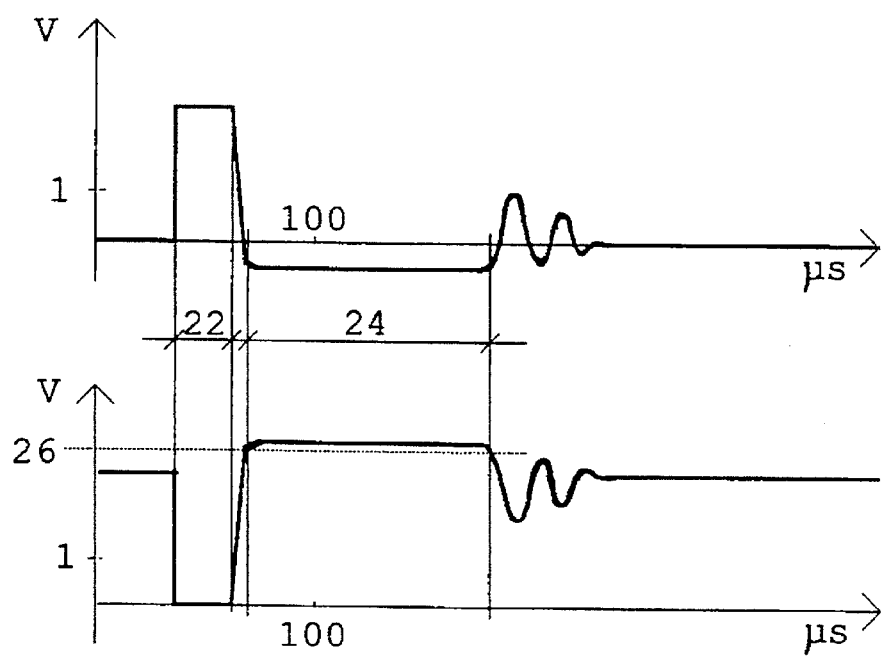
FIG. 4

FIG. 7
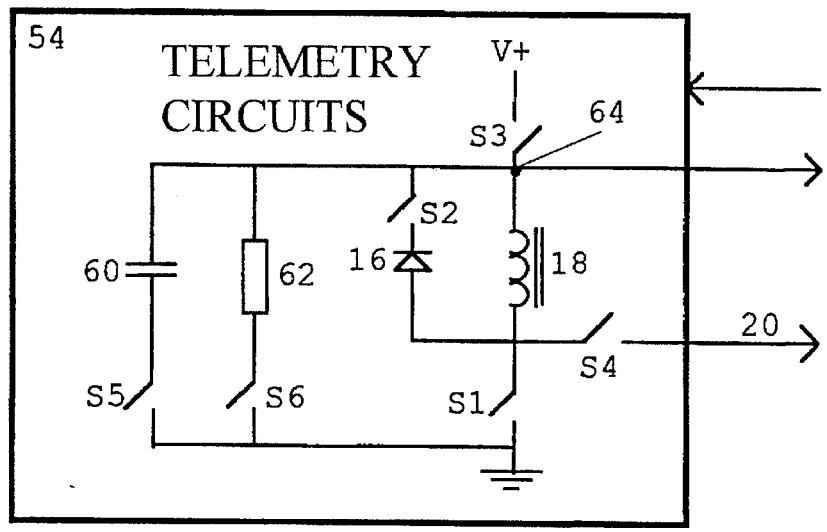
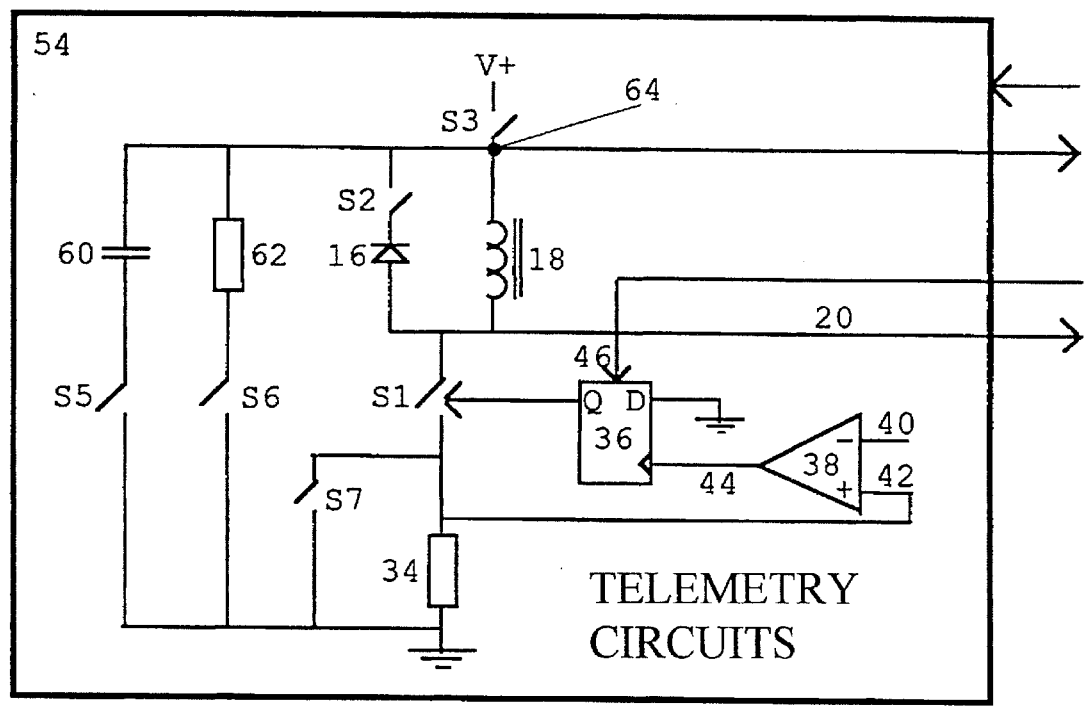
FIG. 8

MAGNETIC FIELD DETECTOR

BACKGROUND OF THE INVENTION

1. Field of the Invention

The present invention relates to a magnetic field detector and a medical implant having a combined telemetry and magnetic field detector unit.

2. Description of the Prior Art

In a medical implant, e.g. a pacemaker, a magnetic field detector is used for non-invasive activation of different implant functions with the aid of a permanent magnet brought close to the implant on the outside of the patient's body. Some of the functions in a pacemaker which can be activated with a magnet are, for example: having the pacemaker disable the demand function so the pacemaker adapts its operation to the capacity of the battery, having the pacemaker operate according to a special, temporary stimulation mode (such as in the presence of tachycardia), and in conjunction with pacemaker programming.

A magnetic field detector intended for a medical implant should be small (the latest generation of pacemakers only weighs about 14 grams), insensitive to bumps and should suit the assembly technique used for other components in the pacemaker.

The detection of magnetic fields outside the implant art in a number of different ways is generally known, e.g. with the aid of reed switches and Hall generators utilizing the Hall effect. The disadvantage of a Hall generator in the context of use in a medical implant is its relatively high energy consumption.

An electronic sensor for detecting static magnetic fields is described in U.S. Pat. No. 4,611,127. The sensor has a conventional resonant circuit with a coil used to sense the presence of a magnetic field whose strength exceeds a defined value. The resonant frequency of the resonant circuit varies according to the strength of the magnetic field. The resonant circuit is activated periodically, and the number of zero crossings of the output signal from the resonant circuit is analyzed in a sensing window of a defined duration. If a given number of zero crossings occurs in the sensing window, this means that the strength of the magnetic field exceeds the defined value.

A magnetic field detector of the conventional kind in the implant art consists of a reed switch. Reed switches, however, are relatively insensitive and rather expensive components which also occupy a relatively large volume in the implant.

To eliminate the need for a reed switch, therefore, utilization of the implant's telemetry unit for detecting the presence of a magnetic field, in addition to performing telemetry functions, has been proposed in recent years.

U.S. Pat. No. 4,541,431 discloses one such proposal with a combined telemetry and magnetic field detector in which magnetic field sensing is performed in the same way as described in U.S. Pat. No. 4,611,127 cited above. The combined unit has a conventional resonant circuit formed by a coil used in telemetry for transmitting and receiving data. The resonant circuit is also used for sensing, in the above-described manner, the presence of a magnetic field whose strength exceeds a defined value.

SUMMARY OF THE INVENTION

An object of the present invention is to provide an improved device, employing fewer components than in known devices, for detecting magnetic fields in general and for detecting magnetic fields near a medical implant in particular.

This object is achieved with a magnetic field detector and a medical implant having a combined telemetry and magnetic field detector of the aforementioned type wherein a coil having a core therein is connected to a source of voltage, with a discharge element such as a diode being connected across the coil. The coil is charged by the voltage source for a defined period of time during a detection mode wherein the presence of a magnetic field is to be determined. The coil is then discharged and a magnetic field indicator measures the discharge time of the coil through the discharge element. The magnetic field indicator generates a signal indicating the presence of a magnetic field if the discharge time is less than a predetermined time threshold value.

The invention utilizes the fact that the inductance of a coil with a core changes in the presence of a magnetic field, because the magnetic field affects the permeability of the core. When a voltage is applied to the coil for a specific period of time and the time it takes the coil to discharge through a diode is measured, the presence of a magnetic field with a defined strength can be detected. This is possible since the coil discharge time is a function of the coils inductance which changes in the presence of a magnetic field. Detection of the presence of a magnetic field is obtained when the discharge time is compared to a time threshold value corresponding to the presence of a magnetic field of a defined strength, and a detection signal is generated if the time is less than the threshold value.

In a first embodiment of the inventive magnetic field detector, the coil's charging time is preset.

In a second embodiment of the invention, the coil's charging time is the time which elapses from the start of charging until the intensity of current through the coil exceeds a preset value.

In a third embodiment of the invention a combined telemetry and magnetic field detector unit is provided in which the coils charging time is preset.

A fourth embodiment of the invention is a telemetry and magnetic field detector in which the coils charging time is the time which elapses from the start of charging until the intensity of current through the coil exceeds a preset value.

DESCRIPTION OF THE DRAWINGS

FIG. 3 is a circuit diagram of a magnetic field sensor according to a second embodiment of the invention.

FIG. 4 shows waveforms for voltage at two points in the inventive magnetic field sensor.

FIG. 7 shows telemetry circuits according to a third embodiment of the invention.

FIG. 8 shows telemetry circuits according to a fourth embodiment of the invention.

DESCRIPTION OF THE PREFERRED EMBODIMENTS

In all the figures, the same reference designations are used for the same or similar elements.

Figure 1:
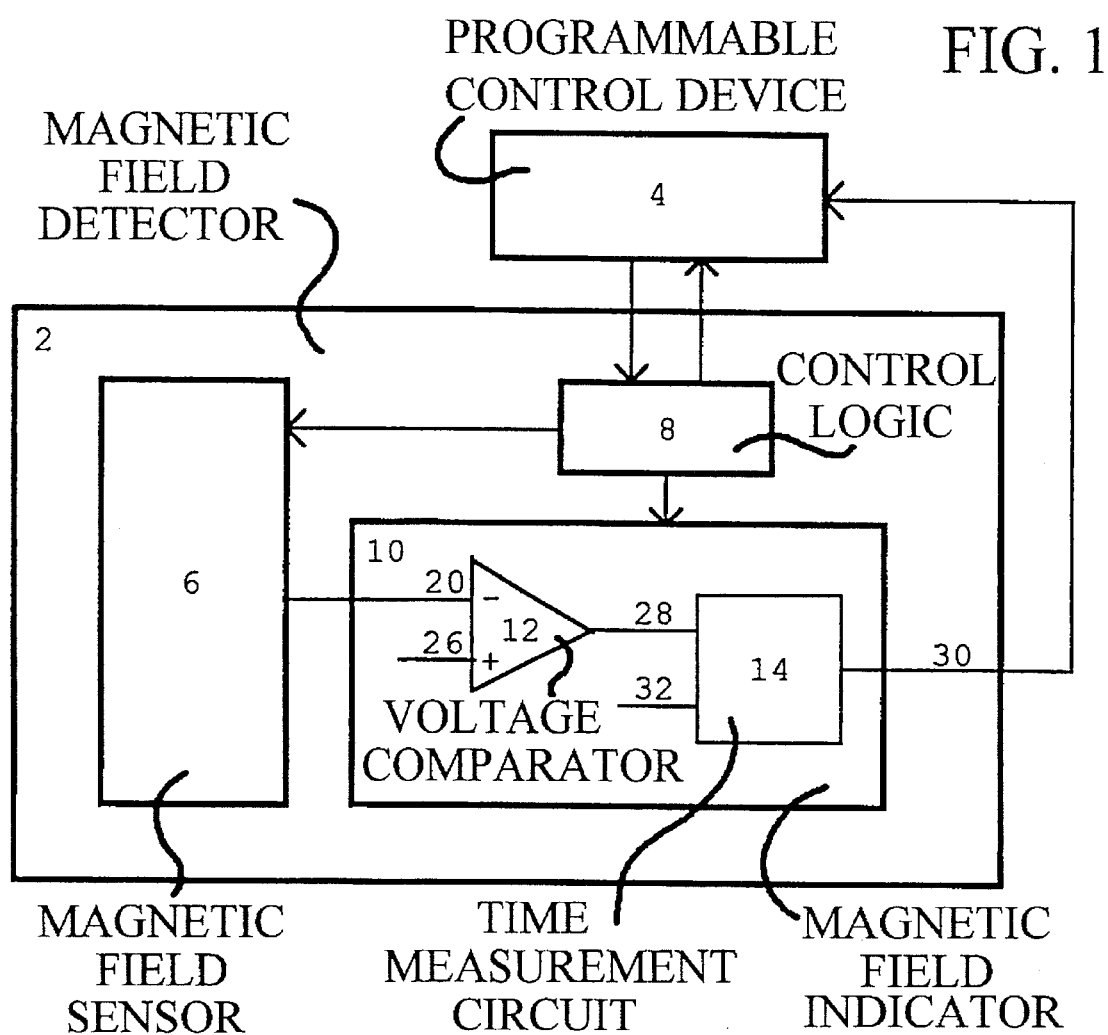
FIG. 1 is a schematic block diagram of a magnetic field detector constructed according to the principles of the present invention.

FIG. 1 shows a magnetic field detector 2 connected to a programmable control device 4. The magnetic field detector 2 comprises a magnetic field sensor 6, control logic 8 and a magnetic field indicator 10. The magnetic field indicator 10 is formed by a voltage comparator 12 and a time measurement circuit 14 connected to the voltage comparator 12.

Figure 2:
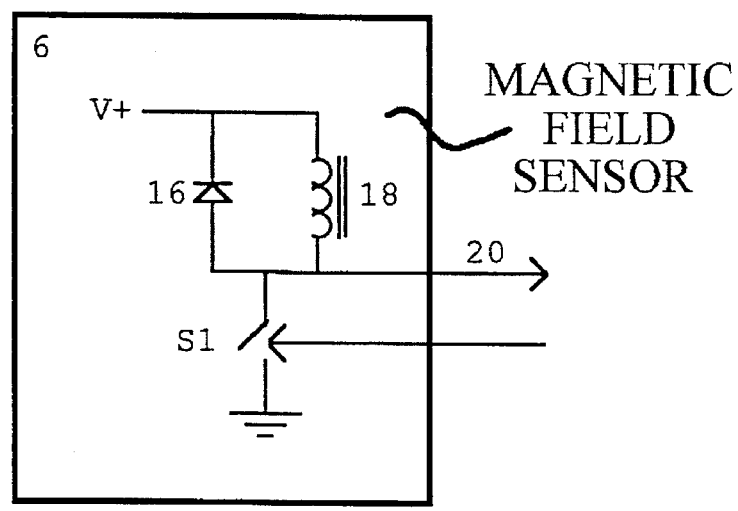
FIG. 2 is a circuit diagram of a magnetic field sensor according to a first embodiment of the invention.

FIG. 2 shows a magnetic field sensor 6 according to a first embodiment. The magnetic field sensor 6 has a source of voltage V+, a discharge element formed by a diode 16, a coil 18 with a core and a switch S1. The diode 16 and the coil 18 are connected in parallel between the voltage V+ and the switch S1 which is connected, in turn, to ground. A measurement signal 20 is tapped between the switch S1 and coil 18 and diode 16, the latter two connected in parallel. The opening and closing of the switch S1 are controlled by the control logic 8.

FIG. 4 shows waveforms for the voltage across the coil 18 (upper curve) and for the measurement signal 20 (lower curve). The vertical axis is for voltage in volts, and the horizontal axis is for time in µs.

Referring to FIGS. 1, 2 and 4, the function of the magnetic field detector 2 will now be described according to the first embodiment.

In its normal state, the switch S1 is open. There is then no voltage across the coil 18, and the measurement signal 20 therefore is at the same potential as the voltage V+. In a mode for determining the presence of a magnetic field with a defined strength, the coil 18 is charged by the source of voltage V+ for a defined period of time (the coil's charging time) 22. This is achieved by closing the switch S1 for the defined period of time 22. During the defined period of time 22, voltage across the coil 18 is equal to the voltage V+. When the switch S1 re-opens, the voltage drops, and the coil 18 discharges through the diode 16. During this discharge period 24, voltage across the coil 18 is equal to the negative of the voltage drop of the diode 16 in the conduction direction. After the discharge time 24, voltage returns to its normal level, i.e. there is no voltage across the coil 18. This return occurs in an oscillatory manner. For measurement of the discharge time, the potential of the measurement signal 20 (the lower curve in FIG. 4) is compared in the voltage comparator 12 to an adjustable voltage threshold value 26. The voltage comparator 12 generates a voltage signal 28 as long as the voltage exceeds the voltage threshold value 26. This voltage signal 28 is sent to the time measurement circuit 14 which emits a detection signal 30 if the duration of the voltage signal 28 is less than an adjustable time threshold value 32. The time threshold value 32 is selected so the presence of a magnetic field of at least a defined strength is detected if the duration of the voltage signal 28 is less than the time threshold value 32. The time measurement circuit 14 can be realized in a number of ways. One way is to measure duration of the voltage signal 28, and this time is then compared to the time threshold value 32, whereupon the detection signal 30 is generated if the duration of the voltage signal 28 is less than the time threshold value 32. Another way is to have a counter count as long as the voltage signal 28 is present. If the count is interrupted before the counter reaches the time threshold value 32, the detection signal 30 is generated.

Typical values are 2.8 V for the voltage V+ and 0.7 V for the voltage drop across the diode 16. The short time in which the coil 18 charges is on the order of some tens of microseconds, e.g. 30 µs. The discharge time 24 of the coil 18 is about 135–145 µs in the absence of a magnetic field and about 120–130 µs in the presence of a magnetic field.

An ordinary permanent magnet, placed at an appropriate distance from the magnetic field detector, is used to achieve a magnetic field with a defined strength. According to one application of the invention, the magnetic field detector 2 is located in a medical implant. The magnet is then applied to the patient's exterior skin surface above the implant. The implant can be a pacemaker, for example. The pacemaker must be able to detect a magnet from a distance up to 40 mm.

According to the above-described first embodiment, the charging time of the coil is therefore predetermined.

According to a second embodiment, the time required for coil charging is the time which elapses from the start of charging until the intensity of current passing through the coil 18 exceeds a preset level. This is achieved in a magnetic field sensor according to FIG. 3.

As in the first embodiment, the magnetic field sensor 6 according to this second embodiment has a source of voltage V+, a diode 16, a coil 18 with a core and a switch S1. This second embodiment also includes a first resistor 34 connected between the switch S1 and ground, a D flip-flop 36 whose Q output terminal controls the switch S1, and a comparator 38 with one input terminal 40 connected to a reference voltage and one input terminal 42 connected between the switch S1 and the first resistor 34. The comparator 38 has an output terminal 44 connected to the clock input terminal of the D flip-flop 38.

In a mode for determining the presence of a magnetic field with a defined strength, the control logic 8 sends a pulse to the reset input terminal 46 on the D flip-flop 36, causing the output terminal Q to go high, thereby closing the switch S1 so charging of the coil 18 starts. The coil continues to charge until the intensity of current through the coil 18 exceeds a defined level. Since current through the coil 18 is the same as the current through the first resistor 34, current intensity is determined by measuring the voltage across the resistor 34. When the potential between the resistor 34 and the switch S1 exceeds the reference voltage 40, the comparator 38 sends a clock signal to the D flip-flop 36, causing the potential on the D input terminal, i.e. the ground potential, to be clocked over to the Q output terminal, and the switch S1 opens.

The intensity of current through the coil 18 is on the order of several hundred µA, e.g. 200–400 µA. The resistance of the first resistor 34 is 500–1000 Ω. This produces a discharge time for the coil 18 of the same magnitude as in the first embodiment. Measurement of the duration of the discharge time 16 is performed in the same way as for the first embodiment. Instead of measuring discharge time, alternatively, the charging time could be use, i.e. the time s, is closed.

According to the first and second embodiments, the magnetic field detector 2 can be used for magnetic field detection in an implantable medical device which could be a pacemaker, a defibrillator, an insulin pump or some other medical device.

Third and fourth embodiments of the invention relate to a combined telemetry and magnetic field detector unit in a medical implant. Again, the implant could also consist of a pacemaker, a defibrillator, an insulin pump or some other medical device.

Figure 5:
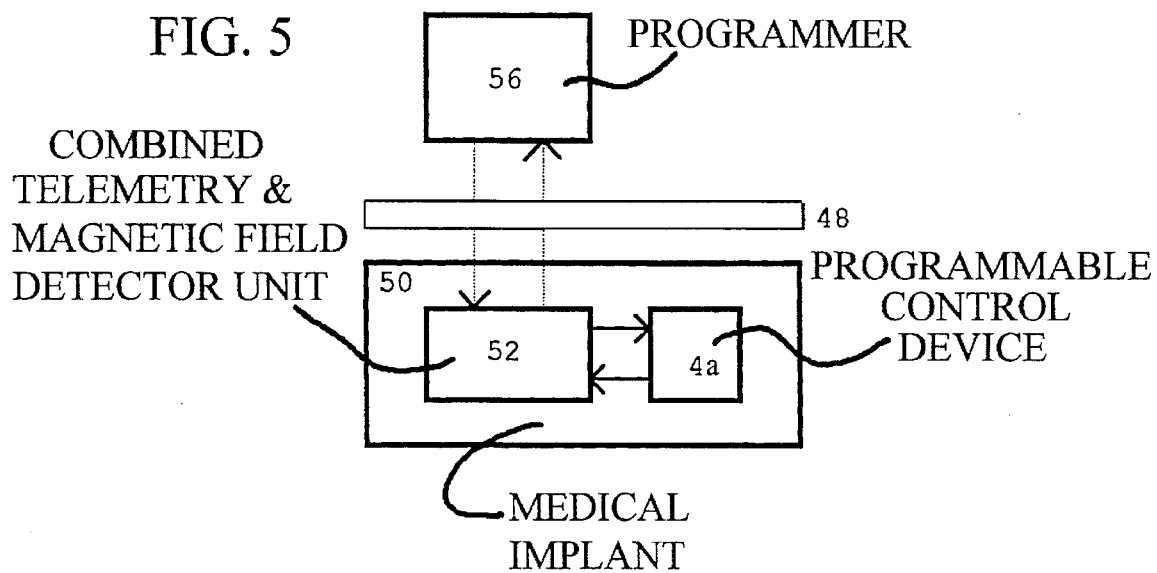
FIG. 5 is a block diagram of a medical implant and a programmer constructed according to the principles of the present invention.

FIG. 5 shows a medical implant 50, inserted under the skin 48, having a programmable control device 4a for control and coordination of the units in the implant 50, and having a combined telemetry and magnetic field detector 52 with, e.g., duplex communications with a programmer 56 placed on the exterior of the skin 48. The programmable control device 4a, in addition to controlling operation of the combined telemetry and magnetic field detector 52, controls all of the functional units for administering therapy in the medical implant 50. Although these units are not shown, they are standard units well-known to those of ordinary skill in the art. If the medical implant 50 is a pacemaker, for example, these units will include electrodes, pacing pulse generating circuitry, and cardiac activity sensing circuitry. If the medical implant 50 is an implantable defibrillator, these functional units will include electrodes, defibrillation pulse generating circuitry, and fibrillation detection circuitry. If the medical implant 50 is a combined pacemaker/cardioverter, the functional units controlled by the control device 4a will be a combination of the aforementioned pacing and defibrillating units. If the medical implant 50 is a medication dosage device, such as an insulin administration device, the functional units will include the medication pump, dosage level control circuitry, reservoir level monitoring circuitry, and possibly glucose level monitoring circuitry.

Figure 6:
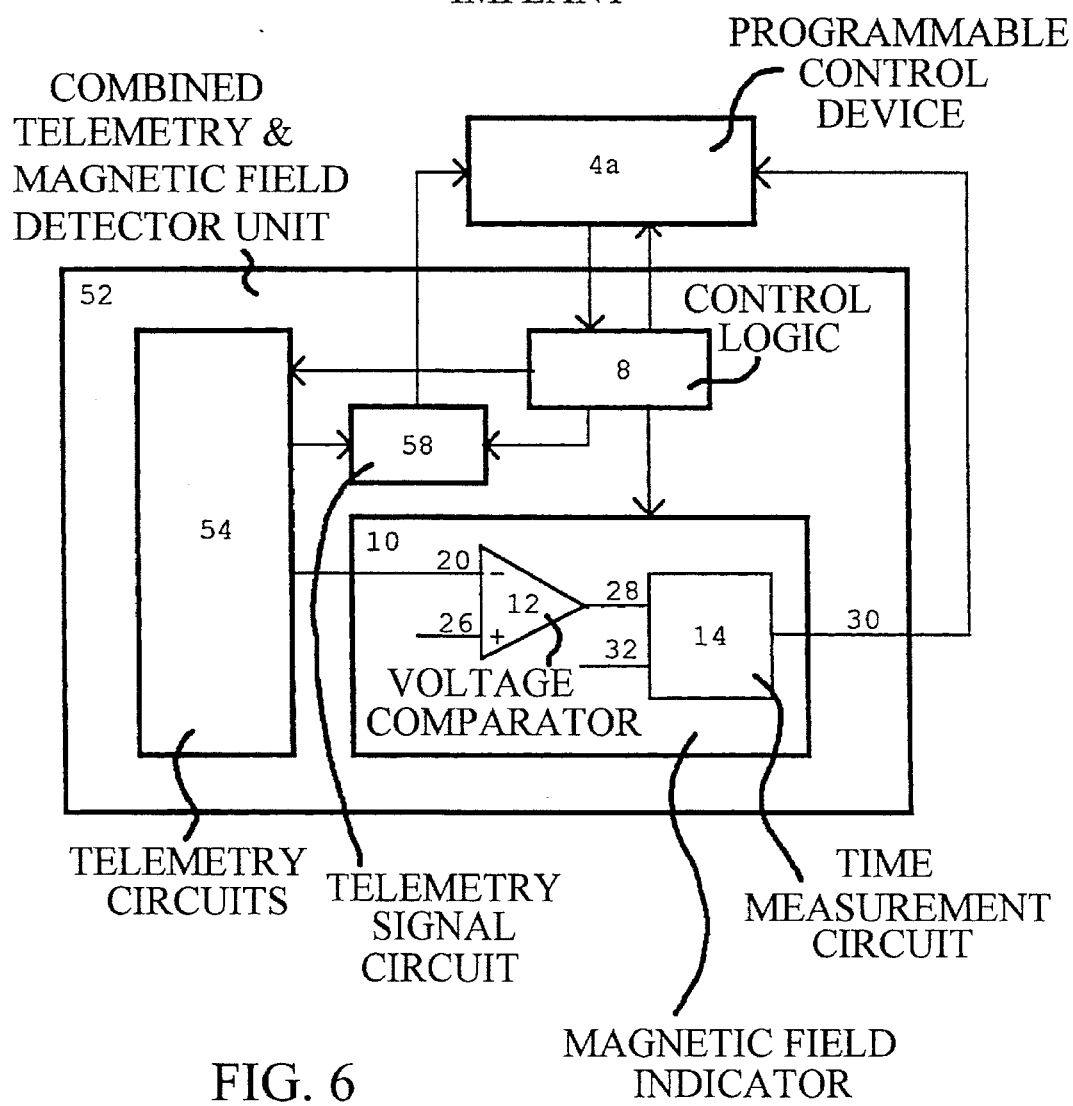
FIG. 6 is a schematic block diagram of a medical implant according to the invention.

FIG. 6 is a block diagram of the combined telemetry and magnetic field detector unit 52, henceforth referred to as the combined unit 52, according to a third embodiment of the invention.

The combined unit 52 includes telemetry circuits 54 used for transmitting and receiving signals to and from the programmer 56 and for sensing magnetic fields, a magnetic field indicator 10 which detects the presence of a magnetic field, a telemetry signal circuit 56 for signals received by the telemetry circuits 54 and control logic 8 for controlling the telemetry circuits 54, the magnetic field indicator 10 and the telemetry signal circuit 58. As in the first and second embodiments, the magnetic field indicator 10 is formed by a voltage comparator 12 and a time measurement circuit 14 connected to the voltage comparator 12.

FIG. 7 shows the telemetry circuits 54 according to the third embodiment of the invention, the telemetry circuits including a source of voltage V+, a diode 16, a coil 18 with a core, a capacitor 60, a second resistor 62, a circuit node 64 and a number of switches S1–S6. With the aid of the switches S1–S6, which are controlled by the control logic 18, the components in the telemetry circuits 54 are enabled according to the function the telemetry circuits 54 is to have at a particular time.

The voltage V+ is connected via a switch S3 to the circuit node 64. The diode 16 and the coil 18 are connected in parallel between the circuit node 64 and the switch S1 which, in turn, is connected to ground. The diode 16 is connected via a switch S2 to the circuit node 64. A measurement signal 20 is tapped between the switch S1 and the coil 18 and diode 16, the latter two connected in parallel, and the measurement signal 20 is supplied to the magnetic field indicator 10 via a switch S4. The capacitor 60 is connected to the circuit node 64 and, via a switch S5, to ground. The second resistor 62 is connected to the circuit node 64 and ground via a switch S6. The telemetry signal circuit 58 is connected to the circuit node 64.

The combined unit 52 senses at a defined interval, for example once a second, whether a magnetic field is present. When such a determination is made, the switches S2, S3 and S4 are closed whereas S5 and S6 are open. Determination of the presence of a magnetic field with a defined strength is performed in the same way as described in conjunction with the first embodiment. Thus, the coil 18 is charged by the source of voltage V+ for a defined period of time 22. This is achieved by closing the switch S1 during the defined period of time 22. Voltage across the coil 18 during the defined period of time 22 is equal to the voltage V+. When the switch S1 re-opens, the voltage drops, and the coil 18 discharges through the diode 16. During the discharge time 24, the voltage across the coil 18 is equal to the negative of voltage drop of the diode 16 in the direction of conduction. After the discharge time 24, voltage returns to its normal level, i.e. there is no voltage across the coil 18. This return occurs in an oscillatory manner. When the discharge time 24 is measured, the potential of the measurement signal 20 (lower curve in FIG. 4) potential is compared in the voltage comparator 12 in the magnetic field indicator 10 to an adjustable voltage threshold value 26. As previously noted, the discharge time 24 of the coil 18 is also measured in the magnetic field indicator 10, a detection signal 30 then being generated if the discharge time 24 is less than a defined time threshold value 32.

When the combined unit 52 is to be used for telemetry, the switches S2 and S4 are open and S1 is closed. In transmission, S5 is closed, the capacitor 60 thus being connected to ground, whereas S6 is open, i.e. the second resistor 62 is not connected to ground. The coil 18 and the capacitor 60 form a resonant circuit which, with an appropriate choice of component values, has a preferred resonant frequency of 8 khz and a high Q value. Switch S3 opens and closes rapidly, so brief pulses are sent to the resonant circuit in which the coil 18 serves as the transmission antenna for the electromagnetic waves. The generated train of pulses comprises the data which are to be transferred to the programmer 56.

When signals are received from the programmer 56, the switches S3 and S5 are open, whereas switch S6 is closed. The coil 18 picks up the signals transmitted by the programmer 56 and sends them, via the telemetry signal circuit 58, to the control device 4. The telemetry signal circuit 58 includes, e.g., a comparator circuit (not shown) in which the signal level for the received signal is compared to a defined threshold level, and only signals exceeding this level are processed. In reception, the second resistor 62 damps the signal so there is no residual voltage on the coil 18 at the start of transmission or reception.

FIG. 8 shows a fourth embodiment of the invention. This embodiment only differs from the above-described third embodiment in two respects. First, the time period in which the switch S1 closes and the coil 18 charges is the same, as in the second embodiment, as the time which elapses from the start of charging until the intensity of current through the coil 18 exceeds a defined level. This is achieved with a D flip-flop 36 and a comparator 38 in the same way as described in conjunction with the second embodiment. Second, a switch S7 is connected across the resistor 34. This switch S7 is only closed during telemetry.

For the combined unit 52 according to the third and fourth embodiments, no determination is made as to whether a magnetic field is present as long as telemetry transmission is in progress. When telemetry has been completed, magnetic field determination starts again, e.g. once a second. This control of the enablement of different functions is exercised by the programmable control device 4.

Although modifications and changes may be suggested by those skilled in the art, it is the intention of the inventors to embody within the patent warranted hereon all changes and modifications as reasonably and properly come within the scope of their contribution to the art.

We claim as our invention:

1. A combined telemetry and magnetic field detector unit for a medical implant, comprising:

a source of voltage;

a telemetry circuit;

a magnetic field detector;

a coil containing a core and connected to said source of voltage and being connected to each of, and shared by, said telemetry circuit and said magnetic field detector;

said telemetry circuit comprising means connected to said coil for transmitting and receiving telemetry signals via said coil;

control means connected to said telemetry circuit and to said magnetic field detector for switching between a telemetry mode for transmitting or receiving said telemetry signals, and a magnetic field detection mode; and said magnetic field detector comprising means connected to said coil and to said source of voltage for, during said magnetic field detection mode, charging said coil with voltage from said source of voltage for a defined period of time and for subsequently discharging said coil, said coil having a discharge time associated therewith, and magnetic field indicator means for measuring said discharge time of said coil and for identifying a presence of a magnetic field in which said coil is disposed, and for generating a detection signal indicating the presence of said magnetic field, if said discharge time is less than a defined time threshold value.

2. A combined telemetry and magnetic field detector for a medical implant as claimed in claim 1 wherein said means for charging and discharging said coil comprises a diode connected across said coil in a circuit path connected to said source of voltage, and switch means for closing said circuit path for charging said coil and for opening said circuit path for discharging said coil across said diode.

3. A combined telemetry and magnetic field detector for a medical implant as claimed in claim 1 wherein said magnetic field indicator means comprises:

means for setting a voltage threshold value;

voltage comparator means connected to said coil and to said means for setting an voltage threshold value for comparing voltage across said coil during discharge of said coil to said voltage threshold value, said voltage comparator means generating an output signal as long as said voltage across said coil exceeds said voltage threshold value; and time measurement means, supplied with said output signal, for emitting said detection signal if a duration of said output signal is less than said time threshold value.

4. A combined telemetry magnetic field detector unit as claimed in claim 1 wherein charging of said coil by said means for charging produces a current through said coil, and wherein said defined period of time for charging said coil comprises a time starting with a beginning of charging of said coil until said current through said coil exceeds a defined current value.

5. A combined telemetry and magnetic field detector unit for a medical implant, comprising:

a source of voltage;

a telemetry circuit;

a magnetic field detector;

a coil containing a core and connected to said source of voltage and being connected to each of, and shared by, said telemetry circuit and said magnetic field detector;

said telemetry circuit comprising means connected to said coil for transmitting and receiving telemetry signals via said coil;

control means connected to said telemetry circuit and to said magnetic field detector for switching between a telemetry mode for transmitting or receiving said telemetry signals, and a magnetic field detection mode; and said magnetic field detector comprising means connected to said coil and to said source of voltage for, during said magnetic field detection mode, charging said coil with voltage from said source of voltage to a predetermined current level and for subsequently discharging said coil, said coil having a charging time associated therewith, and magnetic field indicator means for measuring said charging time of said coil and for identifying a presence of a magnetic field in which said coil is disposed, and for generating a detector signal indicating the presence of said magnetic field, if said charging time is less than a defined time threshold value.

6. A combined telemetry and magnetic field detector for a medical implant as claimed in claim 5 wherein said means for charging and discharging said coil comprises a diode connected across said coil in a circuit path connected to said source of voltage, and switch means for opening said circuit path for charging said coil and for closing said circuit path for discharging said coil across said diode.

7. A combined telemetry and magnetic field detector for a medical implant as claimed in claim 5 wherein said magnetic field indicator means comprises:

means for setting a voltage threshold value;

voltage comparator means connected to said coil and to said means for setting an voltage threshold value for comparing voltage across said coil during discharge of said coil to said voltage threshold value, said voltage comparator means generating an output signal as long as said voltage across said coil exceeds said voltage threshold value; and time measurement means, supplied with said output signal, for emitting said detection signal if a duration of said output signal is less than said time threshold value.

* * * * *